(12) United States Patent
Kassai et al.

(10) Patent No.: US 9,042,959 B2
(45) Date of Patent: *May 26, 2015

(54) MAGNETIC RESONANCE IMAGING APPARATUS AND MAGNETIC RESONANCE IMAGING METHOD

(71) Applicants: KABUSHIKI KAISHA TOSHIBA, Minato-Ku, Tokyo (JP); TOSHIBA MEDICAL SYSTEMS CORPORATION, Otawara-shi, Tochigi-ken (JP)

(72) Inventors: Yoshimori Kassai, Nasushiobara (JP); Shinichi Kitane, Nasushiobara (JP)

(73) Assignees: KABUSHIKI KAISHA TOSHIBA, Tokyo (JP); TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/013,849

(22) Filed: Aug. 29, 2013

(65) Prior Publication Data

US 2014/0002082 A1    Jan. 2, 2014

Related U.S. Application Data

(63) Continuation of application No. 12/169,880, filed on Jul. 9, 2008, now Pat. No. 8,649,846.

(30) Foreign Application Priority Data

Jul. 11, 2007  (JP) .................................. 2007-181894
Jun. 10, 2008  (JP) .................................. 2008-151575

(51) Int. Cl.
*A61B 5/05*      (2006.01)
*G01R 33/567*    (2006.01)
(Continued)

(52) U.S. Cl.
CPC .............. *G01R 33/567* (2013.01); *A61B 5/055* (2013.01); *A61B 5/0816* (2013.01); *A61B 5/486* (2013.01); *A61B 5/7285* (2013.01); *G01R 33/5673* (2013.01)

(58) Field of Classification Search
USPC .................. 600/413, 407, 410; 324/306–309
See application file for complete search history.

(56) References Cited

U.S. PATENT DOCUMENTS 4,746,860 A * 5/1988 Satoh ........................... 324/309
4,905,699 A   3/1990 Sano et al.
(Continued)

FOREIGN PATENT DOCUMENTS

JP    5-305063      11/1993
JP    09-182728      7/1997
(Continued)

OTHER PUBLICATIONS

Examination Report in JP 2008-151575 dated Apr. 2, 2013.
(Continued)

*Primary Examiner* — Tse Chen
*Assistant Examiner* — Joel F Brutus
(74) *Attorney, Agent, or Firm* — Nixon & Vanderhye P.C.

(57) ABSTRACT

A magnetic resonance imaging apparatus includes an acoustic control unit and an image data acquisition unit. The acoustic control unit applies a gradient magnetic field for controlling a sound in synchronization with a signal representing a respiratory body motion. The image data acquisition unit acquires imaging data by subsequently imaging to control the sound and generate image data based on the imaging data.

13 Claims, 6 Drawing Sheets

(51) Int. Cl.
  *A61B 5/055* (2006.01)
  *A61B 5/08* (2006.01)
  *A61B 5/00* (2006.01)

(56) References Cited

U.S. PATENT DOCUMENTS

| | | |
|---|---|---|
| 4,949,042 A | 8/1990 | Kuhara et al. |
| 5,124,649 A | 6/1992 | Denison et al. |
| 5,777,473 A | 7/1998 | Takai et al. |
| 7,254,437 B2 | 8/2007 | Miyazaki |
| 2002/0120190 A1 | 8/2002 | Chang |
| 2002/0167315 A1 | 11/2002 | Kellman et al. |
| 2004/0059213 A1 | 3/2004 | Kassai et al. |
| 2005/0270025 A1 | 12/2005 | Nozaki et al. |
| 2007/0205769 A1 | 9/2007 | Yui et al. |

FOREIGN PATENT DOCUMENTS

| | | |
|---|---|---|
| JP | 09-248286 | 9/1997 |
| JP | 10-323336 | 12/1998 |
| JP | 2002-272704 | 9/2002 |
| JP | 2002-301043 | 10/2002 |
| WO | 2004-080301 A1 | 9/2004 |

OTHER PUBLICATIONS

JP Office Action dated Jun. 3, 2014 in JP 2013-115875.

* cited by examiner

MAGNETIC RESONANCE IMAGING APPARATUS AND MAGNETIC RESONANCE IMAGING METHOD

CROSS-REFERENCE TO RELATED APPLICATIONS

This is a continuation of application Ser. No. 12/169,880 filed Jul. 9, 2008 (now U.S. Pat. No. 8,649,846 issued Feb. 11, 2014), claims priority based on Japanese Patent Application No. 2007-181894 filed Jul. 11, 2007, and Japanese Patent Application No. 2008-151575 filed Jun. 10, 2008, the entire contents of all of which are hereby incorporated by reference.

BACKGROUND

1. Technical Field

The present exemplary embodiment relates to a MRI (magnetic resonance imaging) apparatus and a magnetic resonance imaging method which excites nuclear spins of an object magnetically with an RF (radio frequency) signal having the Larmor frequency and reconstructs an image based on NMR (nuclear magnetic resonance) signals generated due to the excitation and, more particularly, to a magnetic resonance imaging apparatus and a magnetic resonance imaging method which make it possible to suppress or reduce influence of respiratory body motion on imaging.

2. Description of Related Art

Magnetic Resonance Imaging is an imaging method which magnetically excites nuclear spins of an object set in a static magnetic field with an RF signal having the Larmor frequency and reconstructs an image based on an NMR signal generated due to the excitation.

In MRI imaging of the upper abdominal area such as a liver, a fluctuation of an image and an artifact called ghost where the outline of a body surface would be thinly overlapped occur due to respiratory body motion. To avoid these, there is the conventional technique for reducing the influence of respiratory body motion by sorting an encoding order in accordance with a breathing period.

Further, suppression of image degradation is performed by alleviating the object's breathing movement by means of the auto voice function to stabilize a TR (repetition time) (see, for example, Japanese Patent Application (Laid-Open) No. 2001-346773).

When imaging is performed while holding the breath, even if a parallel imaging that is a high-speed imaging technique for acquiring signals with multiple surface coils is applied, an imaging time is limited to 10-30 seconds. An imaging time here becomes TR×(a matrix size in a phase encode direction). Therefore, when imaging is performed while holding the breath, it is difficult to improve a matrix size in a phase encode direction, i.e., a resolution. Moreover, since imaging time is short, SNR (signal-to-noise ratio) is also limited, and imaging with a high SNR and a high resolution for examining detailed disease states is difficult.

Meanwhile, when imaging is performed with the conventional breathing-compensated method, a large difference occurs in image quality of obtained images depending on the stability of a heart rate of the object. This means if both a breathing level of the object and a breathing period stay constant, an ideal synchronous imaging can be performed. However, when breathing of the object becomes erratic, disturbed amplitude and phase because of breathing exist in acquired data even if the conventional correction in a body motion is performed and, therefore, this disturbance appears as an image artifact.

SUMMARY OF EXEMPLARY EMBODIMENTS

The present exemplary embodiment has been made in light of the conventional situations, and it is an object of the present exemplary embodiment to provide a magnetic resonance imaging apparatus and a magnetic resonance imaging method which make it possible to suppress or reduce influence of respiratory body motion on imaging.

The present exemplary embodiment provides a magnetic resonance imaging apparatus comprising: an acoustic control unit configured to apply a gradient magnetic field for controlling a sound in synchronization with a signal representing a respiratory body motion; and an image data acquisition unit configured to acquire imaging data by imaging subsequently to control the sound and generate image data based on the imaging data.

The present exemplary embodiment provides a magnetic resonance imaging apparatus comprising: a correction data acquisition unit configured to acquire correction use data for correcting an influence of a respiratory body motion on image data in synchronization with a signal representing the respiratory body motion; a data acquisition unit configured to acquire imaging data by imaging subsequently to acquiring the correction use data; and a correction unit configured to generate image data having a corrected influence of the respiratory body motion based on the correction use data from the imaging data.

The present exemplary embodiment provides a magnetic resonance imaging apparatus comprising: a correction data acquisition unit configured to acquire correction use data for correcting an influence of a respiratory body motion on image data; an acoustic control unit configured to control a sound by applying a gradient magnetic field with a purpose other than acquiring the correction use data; a data acquisition unit configured to acquire imaging data by imaging subsequently to acquire the correction use data and control the sound; and a correction unit configured to generate image data having a corrected influence of the respiratory body motion based on the correction use data from the imaging data.

The present exemplary embodiment provides a magnetic resonance imaging method comprising: applying a gradient magnetic field for controlling a sound in synchronization with a signal representing a respiratory body motion; and acquiring imaging data by imaging subsequently to control the sound and generate image data based on the imaging data.

The present exemplary embodiment provides a magnetic resonance imaging method comprising: acquiring correction use data for correcting an influence of a respiratory body motion on image data in synchronization with a signal representing the respiratory body motion; acquiring imaging data by imaging subsequently to acquire the correction use data; and generating image data having a corrected influence of the respiratory body motion based on the correction use data from the imaging data.

The magnetic resonance imaging apparatus and the magnetic resonance imaging method as described above make it possible to suppress or reduce influence of respiratory body motion on imaging.

DESCRIPTION OF THE PREFERRED EMBODIMENTS

A magnetic resonance imaging apparatus and a magnetic resonance imaging method according to exemplary embodiments of the present invention will be described with reference to the accompanying drawings.

Figure 1:
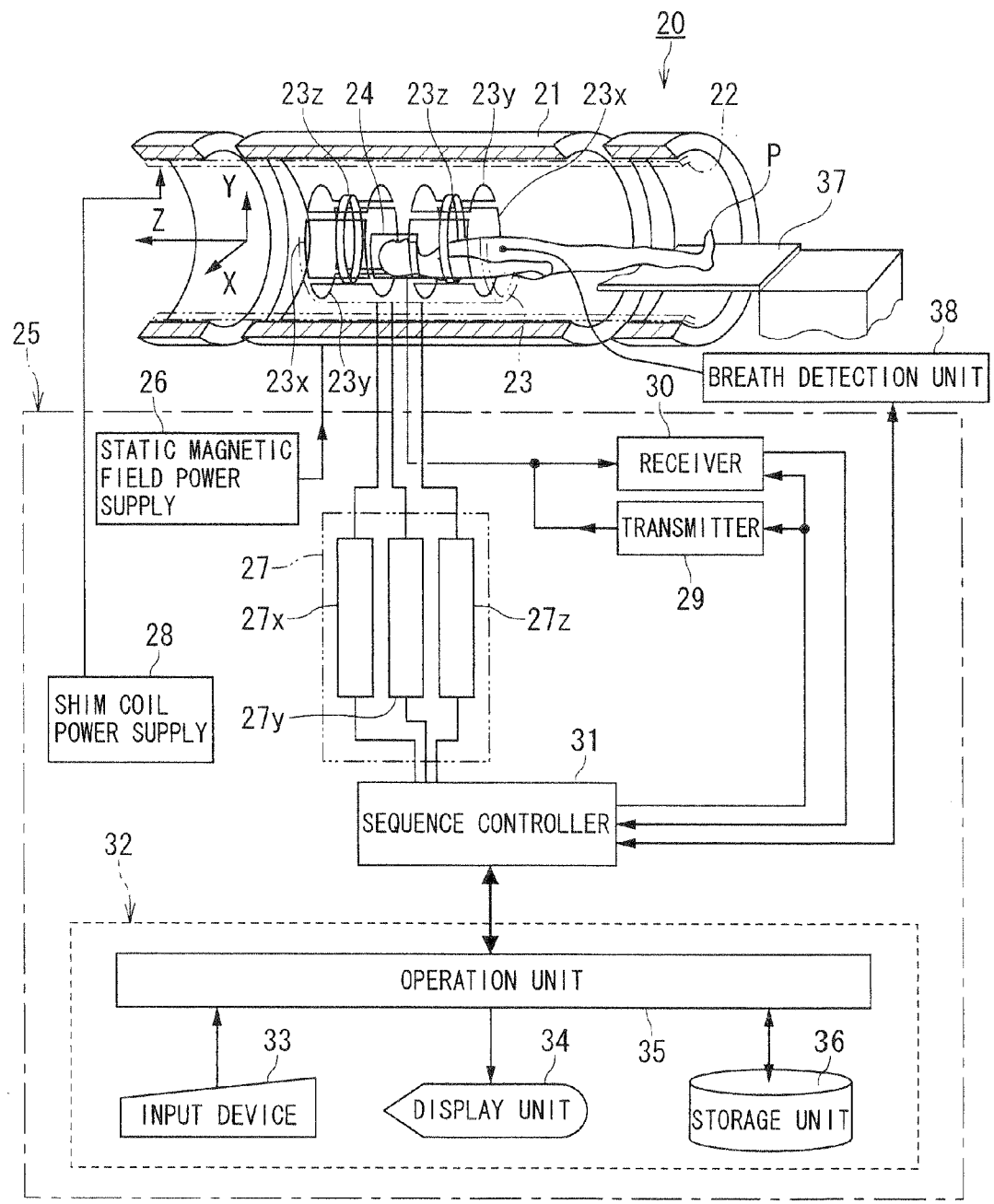
FIG. 1 is a block diagram showing a magnetic resonance imaging apparatus according to an exemplary embodiment of the present invention.

FIG. 1 is a block diagram showing a magnetic resonance imaging apparatus according to an exemplary embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and an RF coil 24. The static field magnet 21, the shim coil 22, the gradient coil 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. Around the bed 37 or the object P, the RF coil 24 may be arranged instead of being built in the gantry.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27, respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit an RF signal given from the transmitter 29 to the object P and receive a MR signal generated due to a nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to store sequence information describing control information needed in order to make the gradient power supply 27, the transmitter 29 and the receiver 30 drive and generate gradient magnetic fields Gx, Gy and Gz in the X, Y and Z directions and an RF signal by driving the gradient power supply 27, the transmitter 29 and the receiver 3Q according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of an NMR signal and A/D conversion to the NMR signal detected in the receiver 30.

The transmitter 29 has a function to give an RF signal to the RF coil 24 in accordance with control information provided from the sequence controller 31. The receiver 30 has a function to generate raw data which is digitized complex number data by detecting an NMR signal given from the RF coil 24 and performing predetermined signal processing and A/D converting to the NMR signal detected. The receiver 30 also has a function to give the generated raw data to the sequence controller 31.

In addition, a breath detection unit 38 for detecting a breath signal from the object P is provided with the magnetic resonance imaging apparatus 20. The breath detection signal acquired by the breath detection unit 38 is outputted to the computer 32 through the sequence controller 31.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 2:
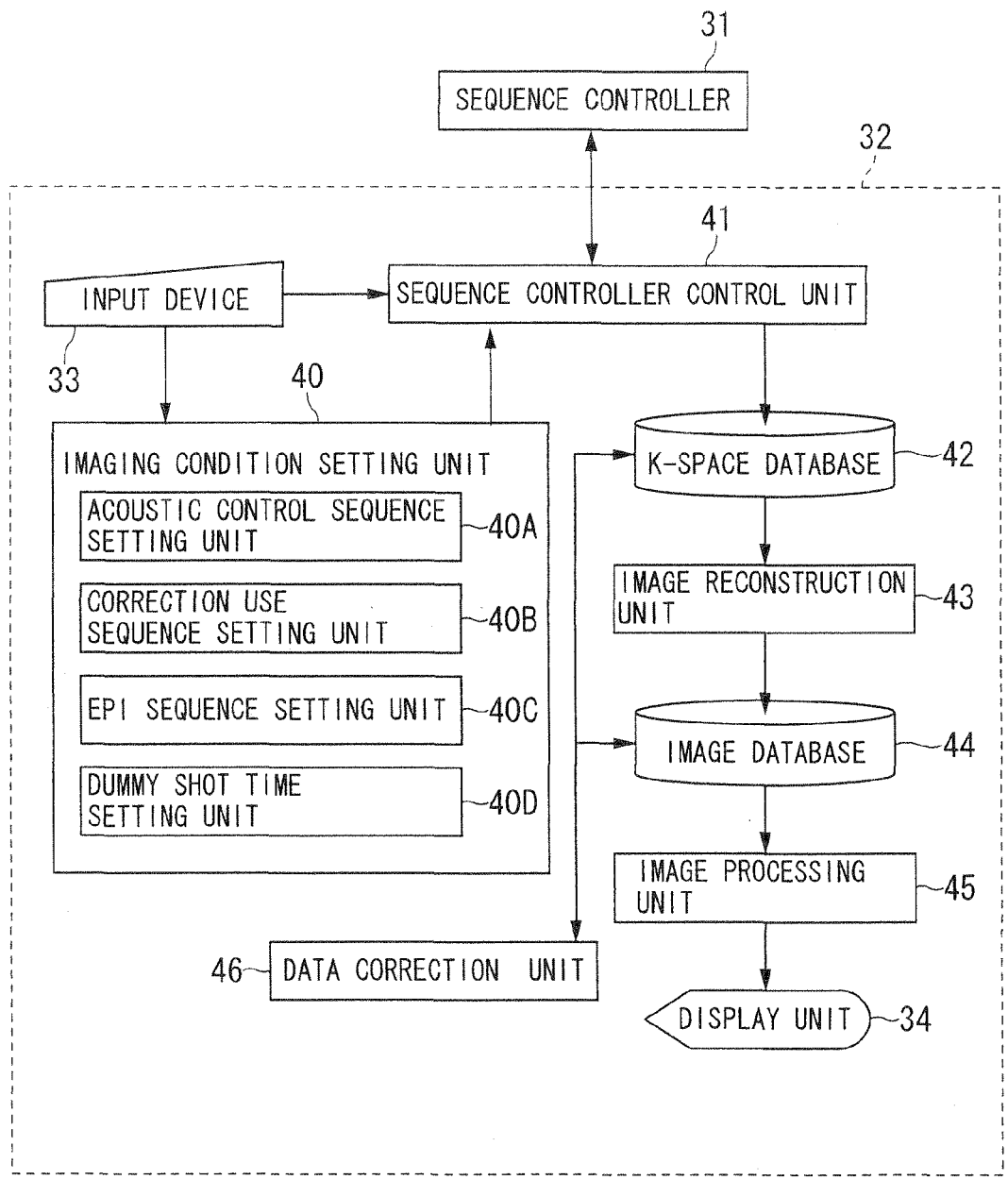
FIG. 2 is a functional block diagram of the computer shown in FIG. 1.

FIG. 2 is a functional block diagram of the computer 32 shown in FIG. 1.

The computer 32 functions as an imaging condition setting unit 40, a sequence controller control unit 41, a K-space database 42, an image reconstruction unit 43, an image database 44, an image processing unit 45 and a data correction unit 46 by program. The imaging condition setting unit 40 includes an acoustic control sequence setting unit 40A, a correction use sequence setting unit 40B, an EPI (echo planar imaging) sequence setting unit 40C and a dummy shot time setting unit 40D.

The imaging condition setting unit 40 has a function to set imaging conditions including a pulse sequence based on instruction information from the input device 33 and to provide the set imaging conditions to the sequence controller control unit 41. Especially, the imaging condition setting unit 40 can set an acoustic control sequence for controlling a sound generated due to a gradient magnetic field, and a correction use sequence for acquiring data for correcting a data deviation due to respiratory body motion of the object P, as well as an imaging sequence for acquiring data for imaging and a dummy shot sequence precedently to an imaging sequence. Further, imaging conditions can be set so as to acquire data under breath synchronization with a breath detection signal obtained by the breath detection unit 38.

The acoustic control sequence setting unit 40A has the function to set an acoustic control sequence. The correction use sequence setting unit 40B has the function to set a correction use sequence. The EPI sequence setting unit 40C has the function to set an EPI sequence as an acoustic control sequence, an imaging sequence and/or a correction use sequence.

The dummy shot time setting unit 40D has the function to set an execution time of a dummy shot sequence. Specifically, the dummy shot time setting unit 40D has the function to set a dummy shot sequence which does not acquire data for imaging between plural imaging sequences to acquire continuously data for imaging in synchronization with a breath detection signal representing a breathing level due to respiratory body motion obtained by the breath detection unit 38, and to elongate and contract the execution time of the dummy shot sequence.

In a dummy shot sequence, a dummy shot by which at least a gradient magnetic field for slice selection is applied and the same RF pulse as that in an imaging sequence is transmitted without disturbing a TR is performed. In a dummy shot sequence, data acquisition may not be performed by applying no gradient magnetic field for readout, or alternatively, acquired data may not be used for imaging though data acquisition is performed while applying a gradient magnetic field for readout.

An acoustic control sequence can be set between dummy shot sequences. In a dummy shot sequence, a gradient magnetic field pulse can be applied arbitrarily with regard to a phase encode axis and another frequency axis when an appropriate slice is selected by the application of a gradient magnetic field pulse for slice selection. In this case, gradient magnetic fields can be set in the positive direction and the negative direction so that the time integration of a gradient magnetic field per TR becomes zero by canceling each other. For this reason, applying gradient magnetic field pulses having various pulse waveforms in various directions and generating gradient magnetic fields can generate a desired sound. That is, adding a gradient magnetic field pulse to a dummy shot sequence can produce an acoustic control sequence. Meanwhile, the sound according to a gradient magnetic field determined for data acquisition is generated in an imaging sequence.

Figure 3:
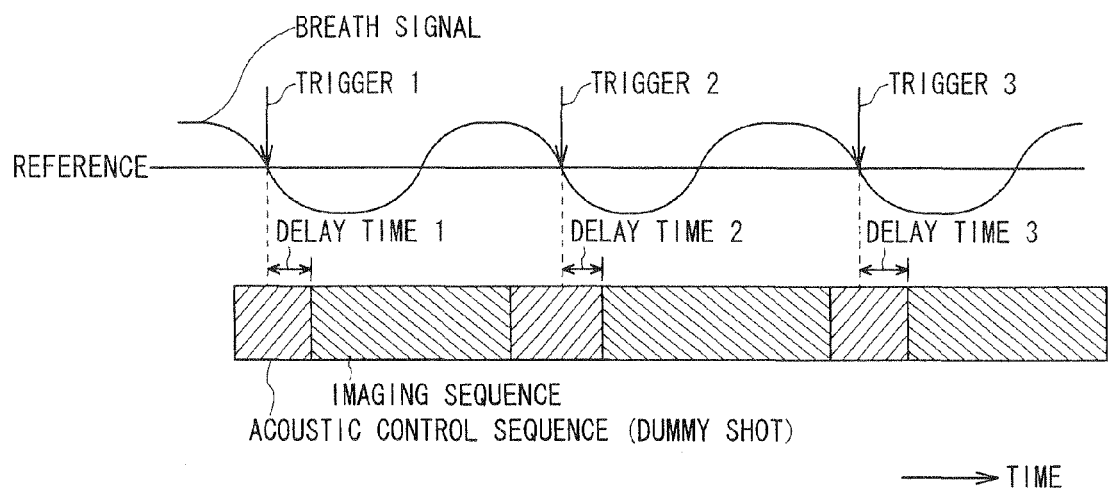
FIG. 3 is a diagram showing timing for performing an acoustic control sequence set by the imaging condition setting unit shown in FIG. 2 in synchronization with breathing.

FIG. 3 is a diagram showing timing for performing an acoustic control sequence set by the imaging condition setting unit 40 shown in FIG. 2 in synchronization with breathing.

In FIG. 3 the abscissa axis denotes time. As shown in FIG. 3, a breath signal that changes periodically can be obtained from the breath detection unit 38. The obtained breath signal is supplied to the computer 32. Then in the acoustic control sequence setting unit 40A, trigger signals (TRIGGER1, TRIGGER2, TRIGGER3, . . . ) can be periodically generated at timings where a level of the breath signal reaches a predetermined reference repeatedly. Moreover, in order to keep the time for breath to stabilize before the start of an imaging sequence, a period from completion of the last imaging sequence to passage of a predetermined delay time (DELAY TIME 1, DELAY TIME 2, DELAY TIME 3, . . . ) after the trigger signal can be a dummy shot sequence for acquiring no data for imaging.

An imaging sequence to acquire data for imaging starts after a dummy shot sequence, and the imaging sequence is set so as to finish earlier than a breathing period which is the interval between trigger signals in consideration of fluctuation of the breath. That is, the dummy shot time setting unit 40D is configured to be able to recognize a roughness of breath by detecting a period of a trigger signal, and adjust a termination time of an imaging sequence as well as a delay time. This can keep a TR of an imaging sequence constant. The dummy shot time setting unit 40D can control to discard the acquired one period data that starts from a trigger signal when receiving the trigger signal during execution of an imaging sequence.

As mentioned above, a dummy shot sequence for acquiring no data for imaging and an imaging sequence for acquiring data for imaging are set periodically and repeatedly. Further, adding a gradient magnetic field pulse to a dummy shot sequence can create an acoustic control sequence. For this reason, an acoustic control sequence and an imaging sequence are performed repeatedly in synchronization with a breath signal generated due to respiratory body motion.

An acoustic control sequence can be created by setting a gradient magnetic field pulse for generating a sound. This means varying intensity and/or a frequency of a gradient magnetic field pulse changes an intensity and a frequency of a sound generated due to application of the gradient magnetic field pulse. Consequently, adjusting intensity and/or a frequency of a gradient magnetic field pulse can control a sound.

Figure 4:
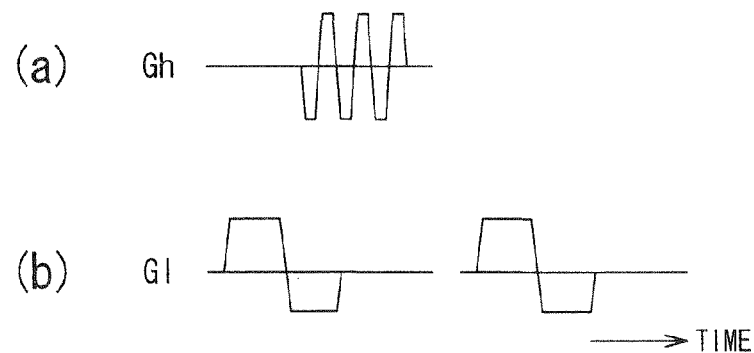
FIG. 4 is a diagram showing an example of acoustic control sequence shown in FIG. 3.

FIG. 4 is a diagram showing an example of acoustic control sequence shown in FIG. 3.

In FIG. 4 the abscissa axis denotes time. A sound differs between a gradient magnetic field pulse Gh such as an EPI sequence that changes at a high frequency as shown in FIG. 4(*a*) and a gradient magnetic field pulse Gl that changes at a low frequency as shown in FIG. 4(*b*). Consequently, for example, a sound can be changed by varying a frequency of a readout gradient magnetic field pulse waveform.

Figure 5:
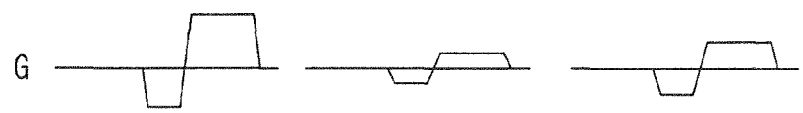
FIG. 5 is a diagram showing another example of acoustic control sequence shown in FIG. 3.

FIG. 5 is a diagram showing another example of acoustic control sequence shown in FIG. 3.

In FIG. 5, the abscissa axis denotes time. As shown in FIG. 5, changing an intensity G of a gradient magnetic field pulse gradually and adjusting its envelope shape can generate a sound having a low frequency.

The acoustic control like this can be performed according to a breath signal. For example, at least one history of an interval of trigger signals is observed. Practically, the most recent three or four histories of the interval of trigger signals are observed. When it is determined that the interval of triggers became longer, the breath is considered to be sluggish and longer. Then, to change one or both of a frequency of a sound and a sound pressure so as to increase encourages the object to accelerate breathing. This means a sound and/or a sound pressure can be determined according to a time variation of the past trigger intervals obtained from a breath signal.

Note that to suppress the generated sound by application of a gradient magnetic field pulse whose intensity is zero is also included in an acoustic control. Further, a tone of sound can be controlled by adjusting an application direction of a gradient magnetic field pulse since respective fixed intensities of gradient magnetic field coils in the x, y and z directions mutually differ.

In the meantime, a level of a breath signal obtained from the object P also changes according to a breathing condition (depth). Therefore, a breath signal is automatically adjusted with a gain to acquire a trigger signal in sufficient accuracy into a breath signal having a certain level. For this reason, a feedback according to a depth of a breath as well as a breath interval can be performed by controlling a sound according to not only a period of a breath signal but also a change history of a gain used for adjustment of the breath signal. In this case, the acoustic control sequence setting unit 40A is configured to obtain a gain from the breath detection unit 38 and set the acoustic control sequence according to the obtained gain.

Performing the above-mentioned acoustic control sequence to control a sound can stabilize a breathing level and a breathing period of the object P further to reduce an image artifact caused by a respiratory body motion. In addition, since the stabilization of breath reduces disturbance of phase and/or amplitude in acquired data, more ideal and favorable correction can be performed in case of performing the after-mentioned correction of body motion.

Note that an arbitrary sequence can be used as an acoustic control sequence and an imaging sequence. For example, a satisfactory effect can be obtained by using a sequence such as a multi-slice sequence under SE (spin echo) method affected strongly by a change of a TR, i.e., of which TR is not over 1000 for acquiring longitudinal relaxation (T1) weighted image data, or a sequential multi-slice sequence under FFE (fast field echo) method whose TR is not over 20 for acquiring pieces of image data one by one.

On the other hand, with an acoustic control sequence or in place of an acoustic control sequence, a correction use sequence can be set between imaging sequences in synchronization with a breath signal. A correction use sequence is a sequence to acquire data for correcting a data deviation due to respiratory body motion of the object P as described above. An FFE sequence and an EPI sequence can be used as a correction use sequence, for example. If a TR of an imaging sequence is long, an EPI sequence gives more satisfactory effect than an FFE sequence.

Figure 6:
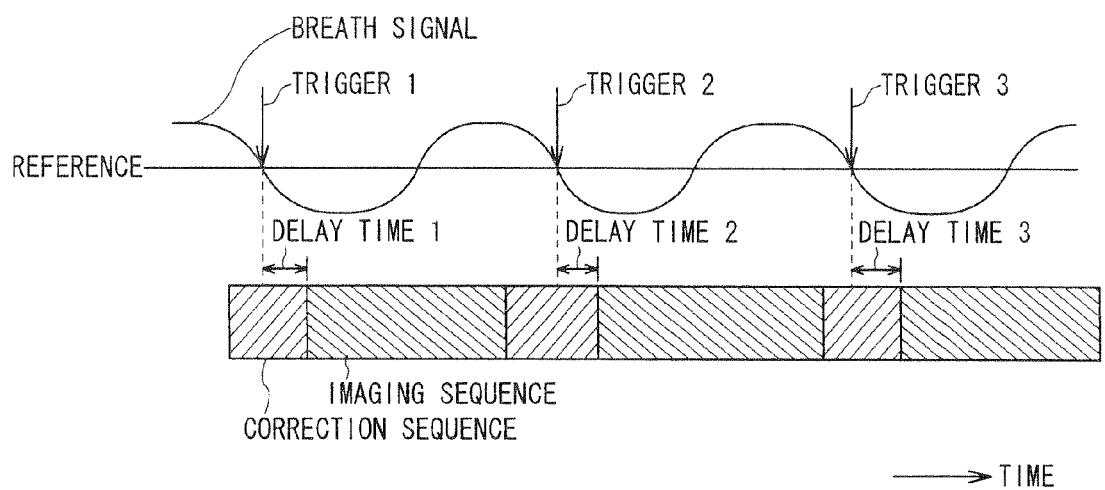
FIG. 6 is a diagram showing timing for performing a correction use sequence set by the imaging condition setting unit shown in FIG. 2 in synchronization with breathing.

FIG. 6 is a diagram showing timing for performing a correction use sequence set by the imaging condition setting unit 40 shown in FIG. 2 in synchronization with breathing.

In FIG. 6 the abscissa axis denotes time. Similarly to the acoustic control sequence shown in FIG. 3, a correction use sequence can be set between imaging sequences in synchronization with a breath signal as shown in FIG. 6. Then, the movement correction of data acquired by a certain imaging sequence can be performed based on data for correction acquired by a correction use sequence before or after the imaging sequence.

Figure 7:
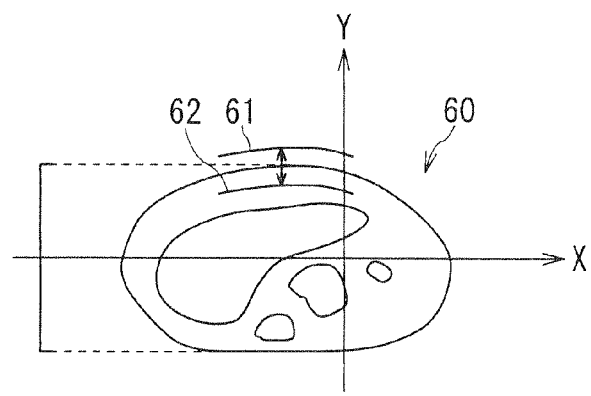
FIG. 7 is a diagram explaining relationship between correction use data acquired by the correction use sequence shown in FIG. 6 and a respiratory motion amount of the object.

FIG. 7 is a diagram explaining relationship between correction use data acquired by the correction use sequence shown in FIG. 6 and a respiratory motion amount of the object P.

FIG. 7 shows a abdominal cross section of the object P. In FIG. 7, the abscissa axis is set as the X-axis and the ordinate axis is set as the Y-axis. An abdomen 60 varies in the Y-axis direction according to a breathing period between the abdomen 61 during inspiration and the abdomen 62 during expiration. For this reason, an amount of movement in the Y-axis direction due to a respiratory body motion needs to be obtained and the movement correction of data needs to be performed according to the amount of movement. Therefore, information regarding a respiratory body motion needs to be acquired as data for correction.

For example, a correction use sequence to acquire one-dimensional (1D) data for correction by applying a readout gradient magnetic field in the Y-axis corresponding to the anterior-posterior direction of the object P can be created.

Figure 8:
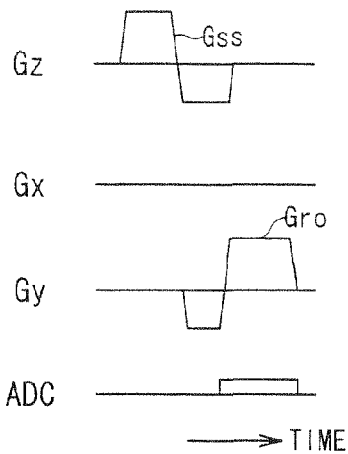
FIG. 8 is a diagram showing an example case of setting one dimensional sequence as the correction use sequence shown in FIG. 6.

FIG. 8 is a diagram showing an example case of setting one dimensional sequence as the correction use sequence shown in FIG. 6.

In FIG. 8, the abscissa axis denotes time, Gz, Gx and Gy denote gradient magnetic fields in Z axis, X axis and Y axis directions, respectively, and ADC denotes correction use data acquired as an echo signal.

As shown in FIG. 8, by setting a correction use sequence for applying a gradient magnetic field pulse Gss for slice selection in the Z-axis direction and a gradient magnetic field pulse Gro for readout in the Y-axis direction, correction use data ADC can be obtained without applying a gradient magnetic field pulse for phase encode. An echo signal obtained by applying a gradient magnetic field pulse in a readout direction and setting a phase encode amount to be zero is sometimes called a navigator echo. This one-dimensional correction use data acquired as K-space (Fourier space) data shifts in phase by an amount depending on the amount of movement in the Y-axis direction due to breath of the object P. Therefore, by regarding the phase shift amount of the correction use data as phase correction data, to correct a phase of K-space data acquired by performing an imaging sequence so that the amount of movement in the Y-axis direction is cancelled can perform movement correction.

However, although in most cases an amount of movement in the Z-axis direction corresponding to the body axis direction of the object P can be calculated with a practical accuracy by acquiring one-dimensional correction use data, an amount of movement in the Y-axis direction corresponding to the anterior-posterior direction of the object P might not be obtained with a practical accuracy by acquiring one-dimensional correction use data. Therefore, a correction use sequence for acquiring two-dimensional image data with a low resolution in the X-axis and the Y-axis directions as correction use data can be created.

Performing two-dimensional acquisition and using image data as the correction use data can calculate a correction amount for correction depending on a positional shift amount in each direction (especially in the Y-axis direction).

Figure 9:
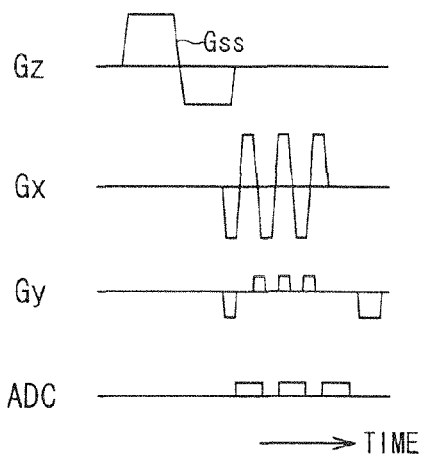
FIG. 9 is a diagram showing an example case of setting two-dimensional sequence as the correction use sequence shown in FIG. 6.

FIG. 9 is a diagram showing an example case of setting two-dimensional sequence as the correction use sequence shown in FIG. 6.

In FIG. 9, the abscissa axis denotes time, Gz, Gx and Gy denote gradient magnetic fields in Z axis, X axis and Y axis directions, respectively, and ADC denotes correction use data acquired as an echo signal.

As shown in FIG. 9, a correction use sequence to obtain two-dimensional image data with a low resolution in the X-axis and the Y-axis direction can be created by an EPI sequence applying a gradient magnetic field pulse for frequency encode whose frequency is higher than that of a gradient magnetic field pulse for frequency encode of an imaging sequence, for example. In this case, an amount of movement of the object P in the Y-axis direction can be obtained from two-dimensional image data as an amount or positional shift, and the positional correction of image data acquired by imaging can be performed by using the obtained amount of positional shift. Further, correction use image data can be temporarily converted into K-space data and a phase of K-space data can be corrected by a phase shift, corresponding to the positional shift, in K-space.

Note that, the movement of the object P can be considered as not only a linear motion of a rigid body accompanied by a translational motion including only a parallel shift and a rotation but also a nonlinear movement of a non-rigid body including scaling (expansion and contraction movement) and shear deformation. When a movement is nonlinear, a correction method, by which K-space is divided according to a size of nonlinear motion measured or predicted based on correction use data in the real space and mutual weighting addition of respective pieces of data corrected by performing different phase correction to each divided K-space is performed, can be employed.

Meanwhile, not only a correction use sequence as described above, but also an acoustic control sequence can be set between imaging sequences. In this case, since a gradient magnetic field pulse shape is limited in order to acquire correction use data, a gradient magnetic field pulse for acoustic control must be set to an extent in which the correction use data can be acquired. For example, when correction use data is acquired under an EPI sequence, the acoustic control can also be performed with acquiring the correction use data by setting a gradient magnetic field pulse such as an end spoiler unnecessary for acquiring the correction use data to the EPI sequence.

Then, other functions of the computer 32 will be described.

The sequence controller control unit 41 has a function for controlling the driving of the sequence controller 31 by giving imaging conditions including a pulse sequence, acquired from the imaging condition setting unit 40, to the sequence controller 31 in response to information instructing scan start from the input device 33. Further, the sequence controller control unit 41 has a function for receiving raw data from the sequence controller 31 and arranging the raw data to K-space formed in the K-space database 42. Therefore, the K-space database 42 stores the raw data generated by the receiver 30 as K-space data. That is, K-space data is arranged in K-space formed in the K-space database 42.

The image reconstruction unit 43 has a function for reconstructing image data, which is real space data, of the object P from K-space data by capturing K-space data from the K-space database 42 and performing image reconstruction processing including FT (Fourier Transformation) to K-space data, and writing the obtained image data to the image database 44. Therefore, the image database 44 stores the image data reconstructed by the image reconstruction unit 43.

The image processing unit 45 has a function for generating two-dimensional image data for displaying by performing necessary image processing to image data read form the image database 44 and displaying the generated image data on the display unit 34.

The data correction unfit 46 has the function to read K-space data or image data acquired as correction use data from the K-space database 42 or the image database 44, then perform a movement correction to K-space data or image data for imaging in an arbitrary method by using correction use data, and to write K-space data or image data after the movement correction in the K-space database 42 or the image database 44. An average (zero-dimensional) phase shift in the real space becomes one-dimensional phase shift in K-space. Further, the positional shift in the real space becomes one-dimensional phase shift in K-space.

Therefore, for example, when one-dimensional or two-dimensional K-space data for correction is acquired by performing a correction use sequence, the phase of K-space data acquired by performance of an imaging sequence can be corrected in the data correction unit 46 with the use of K-space data for correction read from the K-space database 42. More specifically, a phase error $\Delta\phi$ in each shot can be calculated from K-space data for correction acquired by a reference shot n0 and from K-space data for correction acquired by another shot n as shown in expression (1).

$$\phi = 2\pi Y K y$$

$$\phi 0 = 2\pi Y 0 K y$$

$$\Delta\phi = \phi - \phi 0 \quad (1)$$

wherein Y denotes a shift amount due to motion for a shot n and Y0 denotes a shift amount due to motion for reference shot n0.

When the phase error $\Delta\phi$ in each shot is calculated, phase correction can be performed by multiplying $\exp(-\Delta\phi)$ by data for imaging corresponding to each shot.

Meanwhile, when two-dimensional image data for correction is acquired by performing the correction use sequence, in the data correction unit 46, positions of image data acquired by performing the imaging sequence can be also corrected by using correction use image data read from the image database 44. That is, positional shift distances $\Delta Y$ in the respective shots can be obtained based on image data for correction acquired by a reference shot and from image data for correction acquired by another shot. Then, positions can be corrected by subtracting the positional shift distances $\Delta Y$ corresponding to the respective shots from pieces of image data for imaging corresponding to the respective shots respectively. Alternatively, phases can also be corrected by multiplying each pieces of K-space data for imaging by $\exp(-2\pi K y \Delta Y)$.

In addition, a nonlinear motion correction can be performed by dividing K-space and obtaining a phase error corresponding to each divided K-space to perform different phase correction as mentioned above.

Then, the operation and action of a magnetic resonance imaging apparatus 20 will be described.

Figure 10:
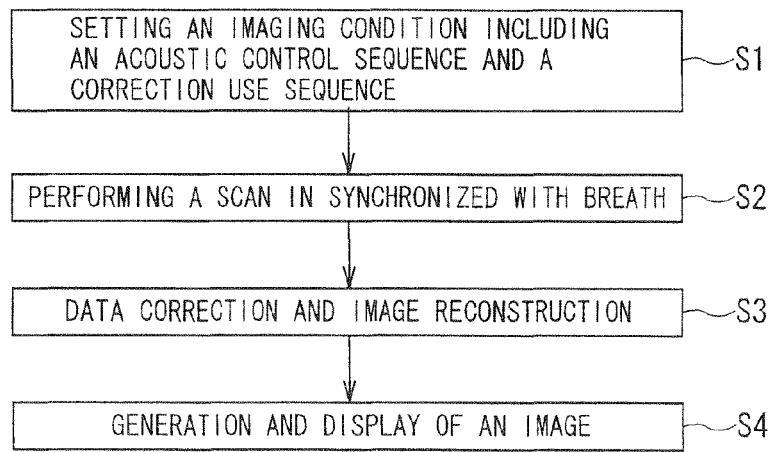
FIG. 10 is a flowchart for generating an image of the object while acoustically controlling and motion correcting regarding respiratory body motion in synchronization with breathing using the magnetic resonance imaging apparatus shown in FIG. 1.

FIG. 10 is a flowchart for generating an image of the object P while acoustically controlling and applying motion correction regarding respiratory body motion synchronized with breathing using the magnetic resonance imaging apparatus 20 shown in FIG. 1.

First, in step S1, the imaging condition is set where an acoustic control sequence and a correction use sequence are performed between imaging sequences performed repeatedly with breath synchronization by the imaging condition setting unit 40. This means the dummy shot time setting unit 40D sets a period of a dummy shot sequence between imaging sequences and the correction use sequence setting unit 40B sets a correction use sequence for acquiring correction use data in the period of the dummy shot sequence as shown in FIG. 8 or FIG. 9. Further, the acoustic control sequence setting unit 40A makes the correction use sequence into an acoustic control sequence by adding a gradient magnetic field pulse for an acoustic control to the correction use sequence. In this instance, when any of the correction use sequence, the acoustic control sequence and the imaging sequence is an EPI sequence, the corresponding EPI sequence is created by the EPI sequence setting unit 40C.

Then in step S2, an imaging scan is performed in synchronization with a breath signal. This means operation instruction is provided from the input unit 33 to the sequence controller control unit 41. Then, an RF signal is transmitted to the object P, and raw data is acquired from the object P.

For this purpose, the object P is set to the bed 37 in advance, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, the input device 33 sends instruction for starting a scan to the sequence controller control unit 41. The sequence controller control unit 41 supplies the imaging conditions including the acoustic control sequence, the correction use sequence and the imaging sequence received from the imaging condition setting unit 40 to the sequence controller 31. Therefore, the sequence controller 31 drives the gradient power supply 27, the transmitter 29, and the receiver 30 in accordance with the imaging conditions received from the sequence controller control unit 41, thereby generating gradient magnetic fields in the imaging area having the set object P, and further generating RF signals from the RF coil 24.

Consequently, the RF coil 24 receives NMR signals generated due to nuclear magnetic resonance in the object P. Then, the receiver 30 receives the NMR signals from the RF coil 24 and generates raw data which is digital data of NMR signals by A/D conversion subsequently to necessary signal processing. The receiver 30 supplies the generated raw data to the sequence controller 31. The sequence controller 31 supplies the raw data to the sequence controller control unit 41. The sequence controller control unit 41 arranges the raw data as K-space data to K-space formed in the K-space database 42.

In such a scan, sound is controlled by performing the acoustic control sequence. For example, the sound changes are approximately synchronized with an interval of breaths. Therefore, breaths are stabilized, and displacements of a breathing period and a breath level of the object P are reduced. As a result, disorders of phase and amplitude in acquired K-space data are reduced.

Then in step S3, movement correction of data based on the correction use data and image reconstruction are performed.

When K-space data is employed as the correction use data, the data correction unit 46 calculates a phase difference corresponding to an amount of movement in the anterior-posterior direction of the object P as a correction coefficient based on the correction use data stored in the K-space database 42. Then, phases of K-space data for imaging acquired by performing the imaging sequence are corrected by the correction coefficients so that the obtained phase difference is cancelled. The phase-corrected K-space data is written in the K-space database 42 again. Subsequently, the image reconstruction unit 43 reconstructs image data by retrieving K-space data after the correction from the K-space database 42 and performing image reconstruction processing. The image data obtained by reconstitution is written in the image database 44.

Meanwhile, when two-dimensional image data with a low resolution is used as correction use data, the image reconstruction unit 43 reconstructs pieces of image data for display and correction by retrieving K-space data before the correction and K-space data acquired as the correction use data from the K-space database 42 and performing image reconstruction processing. The pieces of image data for display and correction obtained by reconstitution are written in the image database 44. Then, the data correction unit 46 calculates a positional displacement amount corresponding to an amount of movement in the anterior-posterior direction of the object P as a correction coefficient based on the correction use image data stored in the image database 44. Then, positions of the image data for display are corrected by the correction coefficients so that the obtained positional displacement amount is cancelled. The image data after the correction is written in the image database 44.

Note that, when a shift due to respiratory body motion is large to make K-space data inappropriate to use for generating image data, it can also be avoided to use a specific piece of K-space data for image reconstruction by removal processing of error data in the data correction unit 46.

Subsequently, in step S4, two-dimensional image data for display is generated from the image data after the movement correction and displayed on the display unit 34. Specifically, the image processing unit 45 retrieves the image data after the movement correction from the image database 44 and generates the two-dimensional image data for display by necessary image processing. Then, the generated image data for display is displayed on the display unit 34.

In this instance, since the image data displayed on the display unit 34 is generated, accompanied by the respiratory movement correction, based on the data acquired under breathing stabilized by the acoustic control, it becomes image data with a reduced artifact caused by respiratory body motion. Therefore, a user can make a diagnosis based on the diagnostic image with a reduced artifact.

That is, the magnetic resonance imaging apparatus 20 as mentioned above is designed to be able to perform stabilization of breath of the object P and/or movement correction of acquired data by performing an acoustic control sequence and/or a correction use sequence precedently to an imaging sequence. Note that, an acoustic control sequence and/or a correction use sequence can be also performed in imaging without breath synchronization. However, improving the stabilization of breath can be expected by performing an acoustic control according to a breath signal. Further, correction use data and data for imaging can be acquired at an appropriate timing and at an appropriate breath signal level by acquiring correction data in synchronization with breath.

For this reason, the magnetic resonance imaging apparatus 20 can perform a longer imaging than breath-holding imaging. Since a breath level and a breathing period become constant by the stabilization of breath of the object P, a higher SNR image can be obtained with a higher resolution by the movement correction especially in case of T1 weighted imaging.

Note that, another artifact reduction technique can be used at the same time. The technique called HIGH SORT or LOW SORT can be cited as an example of an available combination technique of the artifact reduction. In conjunction with these techniques, effect of decreasing of an artifact caused by respiratory body motion can be improved and a high-SNR image can be obtained with a high resolution.

Figure 11:
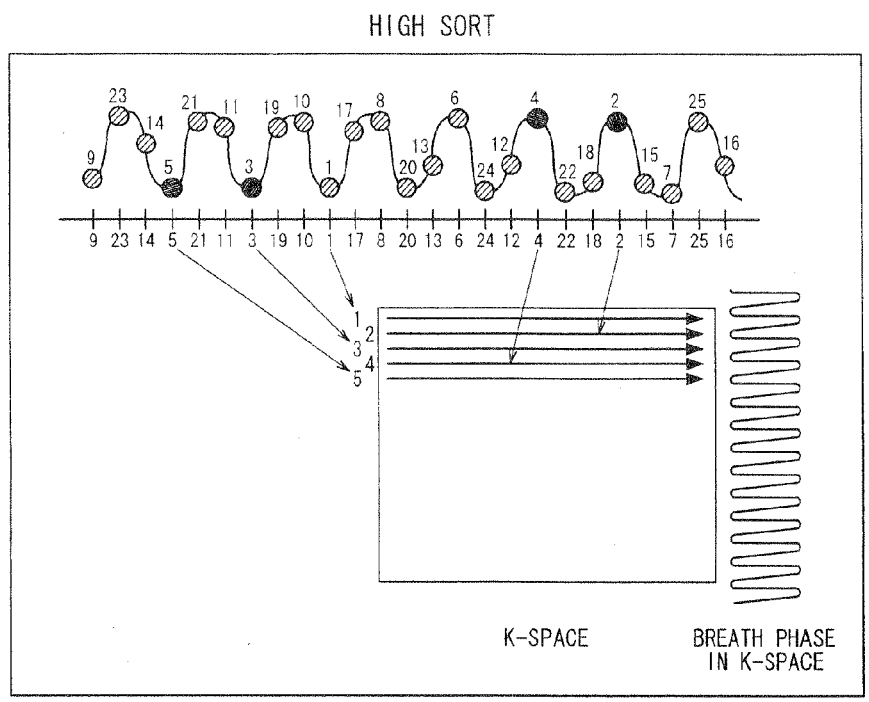
FIG. 11 is a diagram explaining a technique for reducing artifacts referred to as HIGH SORT which can be applied to the magnetic resonance imaging apparatus shown in FIG. 1.

FIG. 11 is a diagram explaining a technique for reducing artifact referred to as HIGH SORT which can be applied to the magnetic resonance imaging apparatus 20 shown in FIG. 1.

As shown in FIG. 11, HIGH SORT is a correction technique for reducing an artifact by sorting the order of phase encoding depending on a breathing period to assign the breathing period to the maximum frequency in K-space. When HIGH SORT is performed, a sequence according to the order of data acquisition is produced in the imaging condition setting unit 40. Then, data sorting is performed in K-space.

Figure 12:
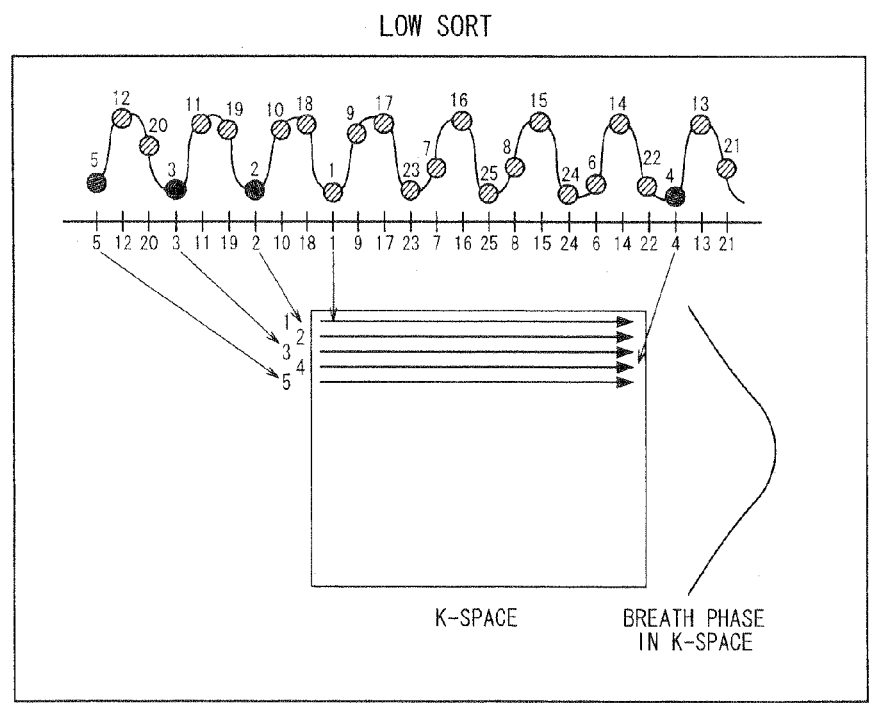
FIG. 12 is a diagram explaining a technique for reducing artifacts referred to as LOW SORT which can be applied to the magnetic resonance imaging apparatus shown in FIG. 1.

FIG. 12 is a diagram explaining a technique for reducing artifact referred to as LOW SORT which can be applied to the magnetic resonance imaging apparatus 20 shown in FIG. 1.

As shown in FIG. 12, LOW SORT is a correction technique for reducing an artifact by sorting the order of phase encoding depending on a breathing period to assign the breathing period to the minimum frequency in K-space. When LOW SORT is performed, a sequence according to the order of data acquisition is also produced in the imaging condition setting unit 40. Then, data sorting is performed in K-space.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
   an assembly of MRI gantry components including static and gradient magnetic field generators and at least one radio frequency (RF) coil coupled to an imaging volume; and
   at least one MRI system control computer and associated program memory coupled to control said gantry components to
   acquire correction data to be used to correct an influence of a respiratory body motion on image data in synchronization with a signal representing the respiratory body motion, the correction data being two-dimensional image data in an X-axis and a Y-axis direction, and the correction data being obtained by applying both readout gradients and phase encode gradients;
   subsequently acquire imaging data; and
   generate corrected image data by correcting for influence of the respiratory body motion based on a position shift in each of the X-axis and Y-axis directions in the correction data.

2. The magnetic resonance imaging apparatus of claim 1, wherein said correction data is acquired using an echo planar imaging sequence.

3. The magnetic resonance imaging apparatus of claim 1, wherein said correction data is acquired using a fast field echo sequence.

4. The magnetic resonance imaging apparatus of claim 1, wherein said correction data is acquired while applying a frequency encode gradient magnetic field for a frequency higher than a frequency encode gradient magnetic field used to acquire the imaging data.

5. The magnetic resonance imaging apparatus of claim 1, wherein said correction data is acquired as either (a) information regarding the respiratory body motion or (b) information regarding a phase of the imaging data.

6. The magnetic resonance imaging apparatus of claim 1, wherein said correction data is acquired during a period that is adjusted in accordance with the signal representing the respiratory body motion while keeping the repetition time for acquiring the imaging data constant.

7. The magnetic resonance imaging apparatus of claim 1, wherein positional correction of the image data is performed by using the position shift in the correction data.

8. The magnetic resonance imaging apparatus of claim 1, wherein the acquired imaging data in K-space is corrected by using a phase shift that is converted from the position shift in the correction data.

9. A magnetic resonance imaging apparatus comprising:
   an assembly of MRI gantry components including static and gradient magnetic field generators and at least one radio frequency (RF) coil coupled to an imaging volume; and
   at least one MRI system control computer and associated program memory coupled to control said gantry components to
   acquire correction data to be used to correct an influence of a respiratory body motion on image data, the correction data being two-dimensional image data in an X-axis and a Y-axis direction, and the correction data being obtained by applying both readout gradients and phase encode gradients;
   control acoustic sound in the MRI gantry by applying a gradient magnetic field with a purpose other than acquisition of the correction data;
   subsequently acquire imaging data; and
   generate corrected image data by correcting for influence of the respiratory body motion based on a position shift in each of the X-axis and Y-axis directions in the correction data.

10. A magnetic resonance imaging method comprising:
    acquiring correction data to be used to correct for influence of a respiratory body motion on image data in synchronization with a signal representing the respiratory body motion, the correction data being two-dimensional image data in an X-axis and a Y-axis direction, and the correction data being obtained by applying both readout gradients and phase encode gradients;
    subsequently acquiring imaging data acquisition of the correction data; and
    generating corrected image data by correcting for influence of the respiratory body motion based on a position shift in each of the X-axis and Y-axis directions in the correction data.

11. The magnetic resonance imaging method of claim 10, wherein the correction data is acquired while applying a frequency encode gradient magnetic field for a frequency higher than a frequency encode gradient magnetic field used to acquire the imaging data.

12. A magnetic resonance imaging apparatus comprising:
    an assembly of MRI gantry components including static and gradient magnetic field generators and at least one radio frequency (RF) coil coupled to an imaging volume; and
    at least one MRI system control computer and associated program memory coupled to control said gantry components to
    acquire correction data to be used to correct an influence of a respiratory body motion on image data in synchronization with a signal representing the respiratory body motion, the correction data being two-dimensional image data in an X-axis and a Y-axis direction, and the correction data being obtained by applying both readout gradients and phase encode gradients; and subsequently acquire imaging data.

13. The magnetic resonance imaging apparatus of claim 12, wherein an order of phase encoding of the imaging data in K-space is sorted based on the correction data.

* * * * *